US012797022B2

(12) United States Patent
Rosenthal et al.

(10) Patent No.: US 12,797,022 B2
(45) Date of Patent: Nov. 17, 2026

(54) AUTONOMOUS LINEAR SCANNING X-RAY SYSTEM FOR SPINAL SURGERY GUIDANCE

(71) Applicant: The General Hospital Corporation, Boston, MA (US)

(72) Inventors: Daniel I. Rosenthal, Boston, MA (US); Kai Yang, Boston, MA (US); Bob Liu, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 139 days.

(21) Appl. No.: 18/840,299

(22) PCT Filed: Feb. 21, 2023

(86) PCT No.: PCT/US2023/062932
§ 371 (c)(1),
(2) Date: Aug. 21, 2024

(87) PCT Pub. No.: WO2023/159245
PCT Pub. Date: Aug. 24, 2023

(65) Prior Publication Data

US 2025/0160773 A1 May 22, 2025

Related U.S. Application Data

(60) Provisional application No. 63/312,350, filed on Feb. 21, 2022.

(51) Int. Cl.
*A61B 6/00* (2024.01)
*G16H 30/20* (2018.01)

(52) U.S. Cl.
CPC .......... *A61B 6/4452* (2013.01); *G16H 30/20* (2018.01)

(58) Field of Classification Search
CPC ........ G16H 30/20; G16H 50/20; G16H 15/00; G16H 30/40; G16H 10/60; G16H 70/00;
(Continued)

(56) References Cited

U.S. PATENT DOCUMENTS 4,809,314 A * 2/1989 Steele .................... G01B 15/04 378/205
7,496,178 B2 * 2/2009 Turner ................ A61B 6/4405 378/102
(Continued)

FOREIGN PATENT DOCUMENTS

CN 107693035 A * 2/2018 .......... A61B 6/4435
KR 10-2008-0073833 A 8/2008
(Continued)

OTHER PUBLICATIONS

International Search Report and Written Opinion for PCT/US2023/062932, mailed Jul. 19, 2023, 11 pages.

*Primary Examiner* — Irakli Kiknadze
(74) *Attorney, Agent, or Firm* — QUARLES & BRADY LLP

(57) ABSTRACT

A compact, portable linear scanning x-ray system includes a physically uncoupled x-ray source and x-ray detector that are each translatable along different respective scanning trajectories. The scanning trajectories may be linear scanning trajectories, which may be parallel linear scanning trajectories. The x-ray source and x-ray detector can be independently moveable. A controller aligns the x-ray source with the x-ray detector and synchronously moves the x-ray source and x-ray detector to obtain an image of an object. Artificial intelligence algorithms can be used to provide for automatic alignment and/or movement of the x-ray source and x-ray detector, which may be based on positioning sensors located on the x-ray source, the x-ray detector, or both.

19 Claims, 4 Drawing Sheets

(58) Field of Classification Search

CPC ..... A61B 6/4429; A61B 6/032; A61B 6/4476; A61B 6/4452; A61B 2034/2055; A61B 6/505; A61B 2034/2048; A61B 6/582; A61B 6/4458; A61B 6/544; A61B 6/4441; A61B 6/0407; A61B 6/5258; A61B 6/5205; A61B 6/465; A61B 6/5235; A61B 6/566; A61B 6/06; A61B 6/4007; A61B 6/4233; A61B 6/542; A61B 6/027; A61B 6/08; A61B 6/4405; A61B 6/587; A61B 6/487; A61B 6/4417; A61B 6/547; A61B 2562/0233; A61B 2560/0487; A61B 6/12; A61B 34/20; A61B 34/00; A61B 34/30; A61B 90/37; A61B 2034/2051; A61B 2034/2059; A61B 2090/376; A61B 2034/2061; A61B 6/4464; A61B 2090/371; A61B 6/5282; A61B 6/4241; A61B 6/4085; A61B 6/486; A61B 6/481; A61B 6/482; A61B 6/4266; A61B 6/483; A61B 6/4071; A61B 6/025; A61B 6/4078; A61B 6/508; A61B 6/4435; A61B 6/04; A61B 6/563; A61B 6/56; A61B 6/54; A61B 2503/40; G01T 1/161; G01T 1/2985; G01T 1/20; G06T 7/0012; G06T 2207/10116; G06T 2207/30168; G06T 2207/20084; G06T 2207/20081; G06T 5/77; G06T 5/60; G06T 5/70; G06T 2207/10121; G06T 2207/10016; G06T 2207/20021; G06T 2207/10081; G06T 7/0014; G06T 7/11; G06T 2207/10088; G06T 2207/30008; G06T 2207/30064; G06T 2207/30096; G06T 2207/30101; G06T 12/10; G06T 12/30; G06T 2207/30004; G06T 11/005; G06T 5/002; G06T 12/20; G06T 2211/421; G06N 3/045; G06N 3/042; G06N 3/08; G06N 3/09; G06N 3/0464; G06N 20/00; G06N 3/084; G06N 5/022; G06F 18/214; G06F 18/254; G06F 18/24; G06V 2201/03; G01N 23/046; G01N 2223/401; G01N 2223/316; G01N 2223/419; G01N 2223/5015; G01N 23/04; G01N 23/223; G21K 1/10; G21K 1/02; G21K 4/00; G01V 5/22; H04N 5/321; A61K 49/0409

USPC ........................................................... 378/62

See application file for complete search history.

(56) References Cited

U.S. PATENT DOCUMENTS

| | | | | |
|---|---|---|---|---|
| 9,861,328 | B2 | 1/2018 | Kang et al. | |
| 10,136,948 | B2 * | 11/2018 | Jensen | A61B 34/30 |
| 10,247,682 | B2 * | 4/2019 | Schlecht | A61B 6/032 |
| 2014/0233698 | A1 * | 8/2014 | Lim | A61B 6/4476 378/197 |
| 2016/0278724 | A1 * | 9/2016 | Papaioannou | A61B 6/102 |
| 2021/0093284 | A1 * | 4/2021 | Sutter | A61B 6/06 |
| 2021/0307710 | A1 | 10/2021 | Kyeong et al. | |
| 2022/0054099 | A1 | 2/2022 | Han et al. | |
| 2022/0245795 | A1 * | 8/2022 | Putha | G06T 7/0012 |

FOREIGN PATENT DOCUMENTS

| | | | | | |
|---|---|---|---|---|---|
| KR | 20080073833 | A * | 8/2008 | A61B 6/4452 |
| WO | WO-2020028704 | A1 * | 2/2020 | A61B 6/587 |
| WO | 2020153692 | A1 | 7/2020 | |
| WO | 2020028422 | A9 | 11/2020 | |

* cited by examiner

AUTONOMOUS LINEAR SCANNING X-RAY SYSTEM FOR SPINAL SURGERY GUIDANCE

CROSS-REFERENCE TO RELATED APPLICATIONS

This application is the national stage entry of PCT/US2023/062932, filed Feb. 21, 2023, which is based on, and claims priority to U.S. Provisional Application Ser. No. 63/312,350, filed Feb. 21, 2022. The contents of these applications are incorporated by reference herein.

BACKGROUND

Operating at the wrong level of the spine is a relatively common error. Surgery performed at the wrong vertebral level does not address the patient's problem, and may cause a variety of additional problems, some of them medical, others economic and psychological. A high percentage of wrong-level surgeries also result in litigation.

To correctly identify an operative level, it is necessary to relate a structure that the surgeon can unambiguously identify in the operative field to the anatomical level seen on pre-operative imaging. Most spine surgeons have developed protocols for securely marking these levels prior to intra-operative imaging. However, there can be significant difficulties with intra-operative imaging. Surgical drapes may cover anatomical land marks, causing problems with x-ray tube centering, angulation, and rotation. Attempts to compensate for these problems using fluoroscopy encounter problems due to small field of view and low image quality. There are large differences in tissue thickness, and therefore x-ray attenuation for different parts of the spine. X-ray scattering from thick body parts (e.g., shoulders, pelvis) greatly diminishes the already-subtle image contrast of spinal vertebra, in some cases making it impossible to confidently count spinal levels.

Currently, intra-operative imaging is typically performed using conventional mobile x-ray and/or C-arm fluoroscopy systems. Occasionally, specialized equipment is used (e.g., O-arm, CT). None of these imaging systems is optimized for intra-operative use, and image quality is frequently poor for spinal surgery. There are also continued technical problems that can make vertebral level identification challenging with conventional imaging systems. For example, scattering remains a drawback that affects image quality.

SUMMARY OF THE DISCLOSURE

The present disclosure provides an x-ray imaging system that includes an x-ray source housed in an x-ray source housing configured to be translated along a first trajectory, and an x-ray detector housed in an x-ray detector housing configured to be translated along a second trajectory that is different from the first trajectory. The x-ray detector housing is physically uncoupled from the x-ray source housing. The x-ray imaging system also includes a controller in communication with the x-ray source and the x-ray detector. The controller is configured to: align the x-ray source with the x-ray detector; and synchronously move the x-ray source along the first trajectory and the x-ray detector along the second trajectory.

In some other aspects, the present disclosure provides an x-ray imaging system that includes an x-ray source module, an x-ray detector module, and a processor in communication with the x-ray source module and the x-ray detector module.

The x-ray source module includes a first housing, an x-ray source housed within the first housing, and a first wheeled base coupled to the first housing. The x-ray detector module includes a second housing, an x-ray detector housed within the second housing, and a second wheeled base coupled to the second housing. The processor is configured to automatically align the x-ray source module with the x-ray detector module by controlling the first wheeled base and the second wheeled base to move the x-ray source module and the x-ray detector module to initial scan positions. The processor is also configured to control the first wheeled base and the second wheeled base to synchronously move the x-ray source module along a first trajectory and the x-ray detector module along a second trajectory that is different from the first trajectory.

DETAILED DESCRIPTION

Figure 1:
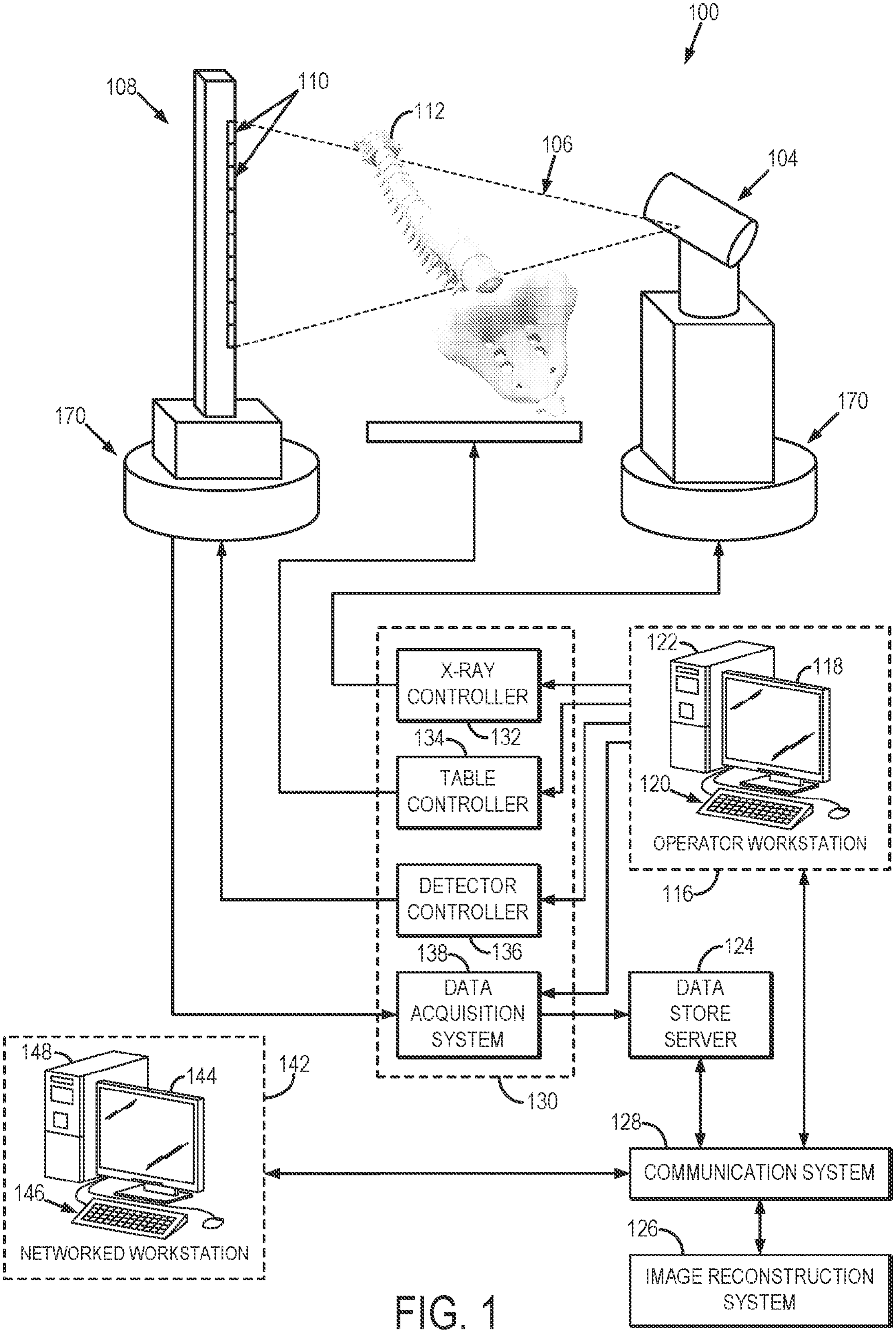
FIG. 1 shows a block diagram of an example linear scanning x-ray imaging system according to some embodiments described in the present disclosure.

Described here are portable linear scanning x-ray systems. In some instances, a "slot scanning" x-ray imaging system for intra-operative use (e.g., for spinal surgery guidance) is provided. In general, the x-ray imaging systems described in the present disclosure are compact and include independently moveable x-ray source and x-ray detector modules. Advantageously, the x-ray source and x-ray detector modules can be moved synchronously with each other, and either autonomously or semi-autonomously. In some configurations, there is no physical connection between the x-ray source module and the x-ray detector module (e.g., there is no wired connection between the two modules).

In some aspects, the two modules can automatically recognize the patient or other imaging object, align to each other, and autonomously move in synchronization to generate an image of the patient or other imaging object. As a non-limiting example, the automatic object recognition can be implemented using an artificial intelligence ("AI") algorithm and/or model, such as a machine learning algorithm and/or model.

The systems and methods described in the present disclosure improve upon previous slot scanning techniques to overcome the issue of poor x-ray image quality for intra-operative guidance. As one advantage over existing operating room image-guidance solutions, the disclosed system significantly improves image quality with greatly reduced scattered radiation, which is the dominant cause of poor image quality for typical radiography or fluoroscopy systems, as well as the absence of parallax and the ability to utilize current modulation. Photon scattering is a major cause of image degradation. It is an advantage of the systems disclosed in the present disclosure to limit scatter in the context of the operating room by acquiring a full-field image by moving a narrow linear detector across the object. The narrow detector lowers the possibility of contamination due to scattered photons. With this configuration, no grid is needed in a scanning system, resulting in a substantial reduction of patient dose (e.g., by a factor of 3-5).

Advantageously, the disclosed systems can be used as a tool to provide confirmation of the alignment and angulation of the entire spine before a surgical procedure begins (e.g., while the patient is in the operating room, and right before the surgical procedure starts), during a procedure, or after a procedure (e.g., while the patient is still in the operating room). Currently, there is no clinically available tool to provide this information. The disclosed systems can provide visual confirmation of the operation site (e.g., the correct spinal level) with external surgical markers, typically surgical clamps, right before the surgical procedure starts. In this way, the disclosed systems can address the existing need for a tool that can provide confirmation for a surgeon to be confident on the correct operation level. Additionally, often times, post-operative imperfections are not discovered until a follow-up visit with the surgeon. In this way, the disclosed systems allow for reduced costs and risk to the patient by avoiding extended and/or repeated surgical procedures, and also the reduce the potential for malpractice claims.

As another advantage, the disclosed system has a compact footprint and thus the flexibility to use in the operating room environment. By using two separate and compact mobile components for the x-ray tube and detector, the footprint of the disclosed imaging system is much smaller than that required by a dedicated computed tomography ("CT") scanner. In general, the disclosed systems can have a footprint that is smaller than a portable x-ray or C-arm fluoroscopy system.

As yet another advantage, the disclosed system has a low cost profile that includes lower equipment and/or operation costs that are more comparable to mobile x-ray than CT scanning. For instance, the disclosed systems can have equipment and/or operation costs on the order of ten percent of those required for a dedicated CT scanner.

It is an aspect of the present disclosure to provide a compact and robust x-ray imaging system that has minimal footprint, much lower cost, and yet much better image quality for spinal surgery guidance. The expected users may include specialists who practice in orthopedic surgery, neurosurgery, radiology, and eventually other surgical specialists. Given its superior image quality, compact design, and low cost, the proposed system can become a standard-of-care equipment in every operating room, in addition to general x-ray/orthopedic clinics or even on mobile ambulances.

Referring now to FIG. 1, an example of an x-ray imaging system 100 in accordance with some embodiments described in the present disclosure is illustrated. The system includes at least one x-ray source 104. The x-ray source 104 projects an x-ray beam 106, which may be a fan-beam or cone-beam of x-rays, towards an x-ray detector 108. The x-ray detector 108 generally includes a number of x-ray detector elements 110.

Advantageously, the x-ray detector 108 can include a narrow linear detector, such as a narrow array of x-ray detector elements 110. As one non-limiting example, the x-ray detector 108 can be a linear detector array having a single row of x-ray detector elements 110. In other examples, the x-ray detector 108 can be an array of x-ray detector elements 110 having 2-10 rows, more than 10 rows, or the like. It is a technical advantage that having a narrow x-ray detector 108 reduces signal contamination due to scattered photons.

In some embodiments, the x-ray detector 108 can be a high sensitivity and fast speed linear array detector. As a non-limiting example, the x-ray detector 108 can be a solid-state linear array detector, such as a gadolinium oxysulfide ("GOS") scintillator-based indirect detector. In an example configuration, the x-ray detector 108 can be a GOS scintillator-based indirect detector composed of a linear array of 640 pixels with a pixel dimension of 0.8 mm×0.7 mm and providing an effective coverage of 51.2 cm.

Together, the x-ray detector elements 110 sense the projected x-rays 106 that pass through a subject 112, such as a medical patient or an object undergoing examination, that is positioned in the x-ray imaging system 100. Each x-ray detector element 110 produces an electrical signal that may represent the intensity of an impinging x-ray beam and, hence, the attenuation of the beam as it passes through the subject 112. In some configurations, each x-ray detector 110 is capable of counting the number of x-ray photons that impinge upon the detector 110.

In general, the x-ray source 104 and the x-ray detector 108 are moveable. As will be described below in more detail, the x-ray source 104 and x-ray detector 108 are coupled to one or more motion modules 170 that move the x-ray source 104 and x-ray detector 108. The x-ray source 104 and x-ray detector 108 can be moved synchronously, or independently of each other, by the motion module(s) 170.

In some embodiments, the x-ray source 104 and the x-ray detector 108 are physically uncoupled from each other. In these instances, the x-ray source 104 and x-ray detector 108 can each be coupled to a separate motion module 170. In other embodiments, the x-ray source 104 and the x-ray detector 108 may be physically coupled, such that each are independently moveable, whether synchronously or otherwise. In these instances, the x-ray source 104 and x-ray detector 108 may be jointly coupled to a single motion module 170, or may be each coupled to a separate motion module 170.

As will be described below in more detail, a motion module 170 can include a wheeled base module that can be rolled or otherwise translated along a surface (e.g., the floor of the operating room). The wheeled base module may be driven or otherwise controlled manually by a user, or may be autonomously or semi-autonomously controlled to move along the first and second trajectories (e.g., via instructions received from the control system 130). Additionally or alternatively, the motion module(s) 170 may include linear tracks (e.g., floor or ceiling mounted tracks to which the x-ray source 104 and the x-ray detector 108 are moveably coupled), rails (e.g., floor or ceiling mounted rails to which the x-ray source 104 and the x-ray detector 108 are moveably coupled), non-motorized wheeled platforms, or other such configurations for moving the x-ray source 104 and the x-ray detector 108 along the first and second trajectories In some instances, the imaging system 100 includes an operator workstation 116, which typically includes a display 118; one or more input devices 120, such as a keyboard and mouse; and a computer processor 122. The computer processor 122 may include a commercially available programmable machine running a commercially available operating system. The operator workstation 116 provides the operator interface that enables scanning control parameters to be entered into the imaging system 100.

The operator workstation 116 may be in communication with a data store server 124 and an image reconstruction system 126. By way of example, the operator workstation 116, data store sever 124, and image reconstruction system 126 may be connected via a communication system 128, which may include any suitable network connection, whether wired, wireless, or a combination of both. As an example, the communication system 128 may include both proprietary or dedicated networks, as well as open networks, such as the internet.

The operator workstation 116 is also in communication with a control system 130 that controls operation of the imaging system 100. In some instances, the control system 130 can be implemented as a part of the operator workstation 116. The control system 130 generally includes an x-ray controller 132, a table controller 134, a detector controller 136, and a data acquisition system ("DAS") 138. The x-ray controller 132 provides power and timing signals to the x-ray source 104 and can control the motion of the x-ray source 104 along the first trajectory. The detector controller 136 controls the motion of the x-ray detector 108 along the second trajectory. The x-ray controller 132 and the detector controller 136 can also control the alignment and synchronous motion of the x-ray source 104 and x-ray detector 108 with each other.

In some instances, a central controller can control the operation of both the x-ray source 104 and x-ray detector 108. As described above, in some instances, the alignment and motion of the x-ray source 104 and x-ray detector 108 can be facilitated using AI algorithms or models, such as machine learning algorithms or models (e.g., that may implement computer vision or the like). The table controller 134 controls a table 140 to position the subject 112.

The DAS 138 samples data from the detector elements 110 and converts the data to digital signals for subsequent processing. For instance, digitized x-ray data is communicated from the DAS 138 to the data store server 124. The image reconstruction system 126 then retrieves the x-ray data from the data store server 124 and reconstructs an image therefrom. The image reconstruction system 126 may include a commercially available computer processor, or may be a highly parallel computer architecture, such as a system that includes multiple-core processors and massively parallel, high-density computing devices. Optionally, image reconstruction can also be performed on the processor 122 in the operator workstation 116. Reconstructed images can then be communicated back to the data store server 124 for storage or to the operator workstation 116 to be displayed to the operator or clinician.

The imaging system 100 may also include one or more networked workstations 142. By way of example, a networked workstation 142 may include a display 144; one or more input devices 146, such as a keyboard and mouse; and a processor 148. The networked workstation 142 may be located within the same facility as the operator workstation 116, or in a different facility, such as a different healthcare institution or clinic.

The networked workstation 142, whether within the same facility or in a different facility as the operator workstation 116, may gain remote access to the data store server 124 and/or the image reconstruction system 126 via the communication system 128. Accordingly, multiple networked workstations 142 may have access to the data store server 124 and/or image reconstruction system 126. In this manner, x-ray data, reconstructed images, or other data may be exchanged between the data store server 124, the image reconstruction system 126, and the networked workstations 142, such that the data or images may be remotely processed by a networked workstation 142. This data may be exchanged in any suitable format, such as in accordance with the transmission control protocol ("TCP"), the internet protocol ("IP"), or other known or suitable protocols.

Figure 2A:
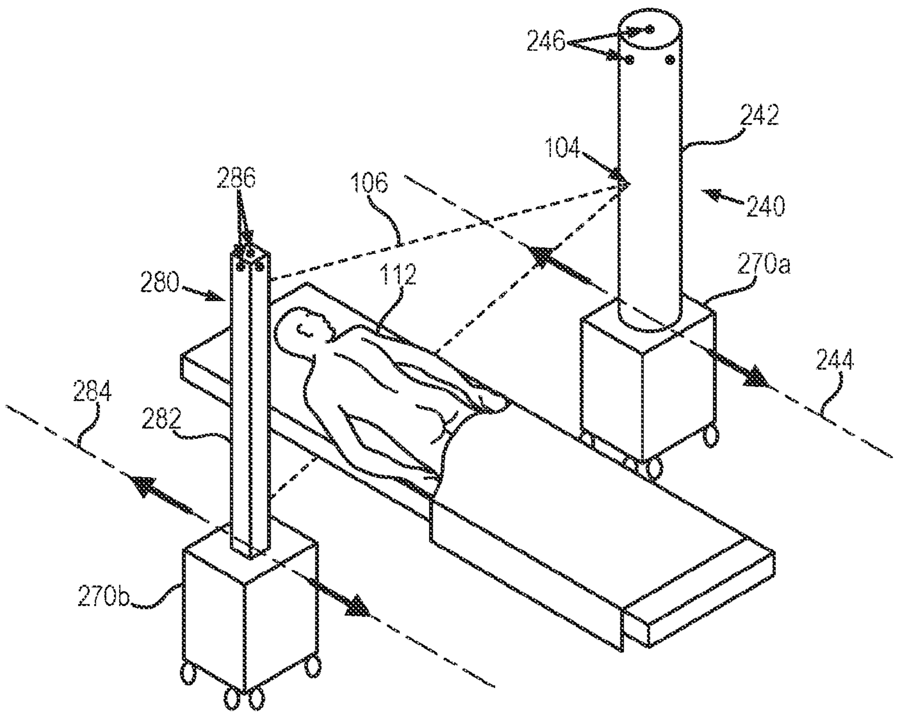
FIG. 2A shows an example linear scanning x-ray imaging system having physically uncoupled x-ray source and detector modules, according to some embodiments described in the present disclosure.

As noted above, in some configurations, the x-ray source 104 and the x-ray detector 108 are physically uncoupled from each other, such that the motion of each of the x-ray source 104 and the x-ray detector 108 can be independently controlled. An example of such a configuration is illustrated in FIG. 2A.

The imaging system 200 includes a moveable x-ray source module 240 and a moveable x-ray detector module 280 that is physically uncoupled from the x-ray source module 240. The x-ray source module 240 includes a housing 242 that contains or otherwise supports an x-ray source 104, whereas the x-ray detector module 280 includes a housing 282 that contains or otherwise supports an x-ray detector 108. In the illustrated embodiment, the x-ray source module 240 is coupled to a first motion module **270*a* and the x-ray detector module 280 is coupled to a second motion module 270*b***.

Figure 2B:
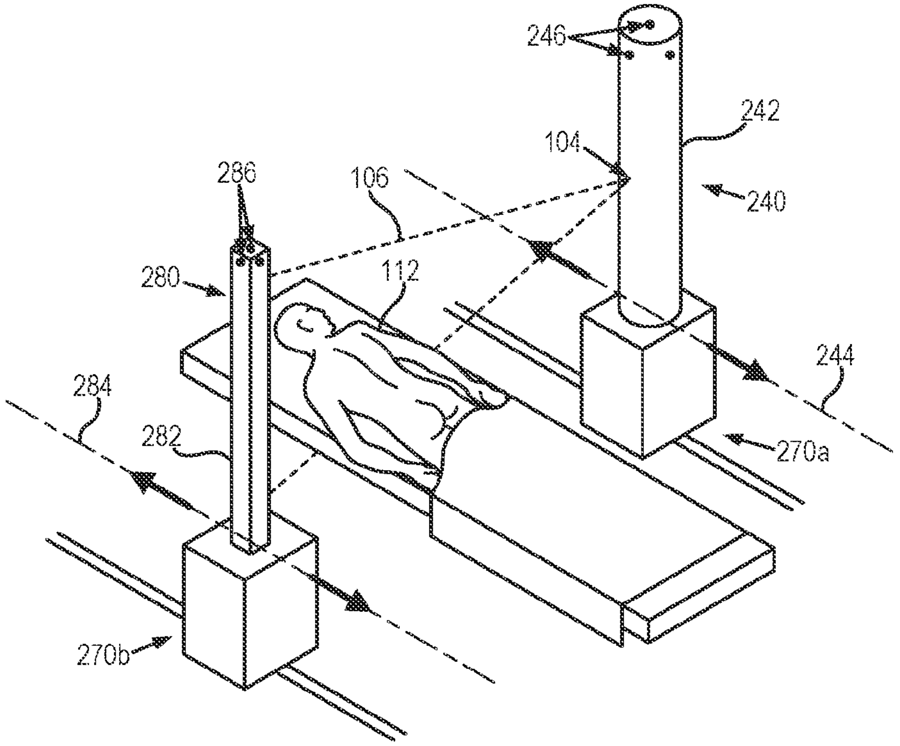
FIG. 2B shows an example linear scanning x-ray imaging system having physically uncoupled x-ray source and detector modules, according to some additional embodiments described in the present disclosure.

As described above, the first motion module **270*a* is moveable so as to move the x-ray source module 240, and thus the x-ray source 104, along a first trajectory 244. Similarly, the second motion module 270*b* is moveable so as to move the x-ray detector module 280, and thus the x-ray detector 108, along a second trajectory 284. In the illustrated embodiment, the first and second motion modules 270*a*, 270*b* are wheeled base modules. In other embodiments, such as the embodiment illustrated in FIG. 2B, the first and second motion modules 270*a*, 270*b* can be implemented as rails and/or tracks, along which the x-ray source module 240 and x-ray detector module 280** can be moved.

During a scan to acquire x-ray projection data, the x-ray source module 240, and thus x-ray source 104, moves along the first trajectory 244 and the x-ray detector module, and thus x-ray detector 108, moves along the second trajectory 284, that is different from the first trajectory. The first and second trajectories 244, 284 may both be linear trajectories. The first and second trajectories 244, 284 may be parallel to each other. In some embodiments, the first and second trajectories 244, 284 may be oriented along the same direction, such that both the x-ray source module 240 and the x-ray detector module 280 are moved along the same direction (e.g., along the longitudinal direction) during a scan, albeit along different trajectories (e.g., a first trajectory 244 on one side of the subject 112 and a second trajectory 284 on another side of the subject 112). In other embodiments, the first and second trajectories 244, 284 may be oriented along different directions (e.g., first and second directions, respectively), such that the x-ray source module 240 and the x-ray detector module 280 are moved along different directions during a scan. For example, the x-ray source module 240 and the x-ray detector module 280 may in some configurations be rotated or partially rotated about a portion of the subject 112, such that the x-ray source 104 and the x-ray detector 108 move in different directions about the subject 112.

Advantageously, the x-ray source module 240 and x-ray detector module 280 can be autonomously controlled and/or operated. For instance, the x-ray source module 240 and x-ray detector module 280 may each have an onboard controller or processor that controls the independent and autonomous operation of the x-ray source module 240 and x-ray detector module 280. In this way, the x-ray source module 240 and x-ray detector module 280 can be viewed as autonomous robotic imaging system components that are capable of automatically aligning with each other, automatically detecting the subject to be imaged (and their positions relative to the subject), and moving along the first and second trajectories while scanning the subject to acquire x-ray projection data, from which images of the subject can be reconstructed.

Although physically uncoupled in the sense that the x-ray source module 240 and the x-ray detector module 280 can be moved independently of each other, in some embodiments the x-ray source module 240 and the x-ray detector module 280 can be in a wired communication with each other, such that a wire or other physical electrical connection exists between the x-ray source module 240 and the x-ray detector module 280. For example, the x-ray source module 240 and the x-ray detector module 280 can be in electrical communication with each other via one or more wires connecting the x-ray source module 240 and the x-ray detector module 280. In these instances, the synchronous motion of the x-ray source module 240 and the x-ray detector module 280 (and thus, synchronous motion of the x-ray source 104 and x-ray detector 108) can be controlled based on electrical signals shared between the x-ray source module 240 and the x-ray detector module 280 (e.g., clock signals, trigger signals, and so on). The synchronous motion of the x-ray source module 240 and the x-ray detector module 280 in these configurations can, therefore, be provided by communication between the x-ray source module 240 and the x-ray detector module 280, and not a physical coupling between the x-ray source module 240 and the x-ray detector module 280 that transferring motion from one component to the other.

Additionally or alternatively, the x-ray source module 240 and the x-ray detector module 280 can be in wireless communication with each other. In these instances, the x-ray source module 240 and x-ray detector module 280 may wirelessly communicate with each other to provide synchronous motion. For instance, electrical signals wirelessly shared between the x-ray source module 240 and the x-ray detector module 280 (e.g., clock signals, trigger signals, and so on) can be used to provide for and maintain synchronous motion of the x-ray source module 240 and x-ray detector module 280.

The x-ray source module 240 includes source position sensors 246, and similarly the x-ray detector module 280 includes detector position sensors 286. The source position sensors 246 can be coupled to the housing 242 (e.g., arranged on, mounted to, or otherwise coupled to the housing 242) of the x-ray source module 240, and similarly the detector position sensors 286 can be coupled to the housing 282 (e.g., arranged on, mounted to, or otherwise coupled to the housing 282) of the x-ray detector module 280. The positioning sensors can record or otherwise measure the position of the source and/or detector modules, allowing for alignment of the x-ray source module 240 relative to the x-ray detector module 280. Additionally, the position data recorded by or otherwise measured using the positioning sensors 246, 286 can be used to synchronize the motion of the x-ray source module 240 and the x-ray detector module 280 (e.g., by tracking the positions of the source and detector modules can maintaining a proper alignment of the modules are they are moved along the first and second trajectories).

The source and detector positioning sensors 246, 286 may be active positioning sensors, passive positioning sensors, or combinations thereof. As an example, active positioning sensors include positioning sensors that transmit a signal that is used to determine the position of the transmitting sensor, the receiving sensor, or both. Active positioning sensors can include RF transmitters, such as those that may transmit via Bluetooth®, Wi-Fi®, Zigbee®, cellular, or other proprietary protocols; ultrasound transceivers; inertial sensors; and the like. As an example, passive positioning sensors include positioning sensors that are detected and tracked by an external system to determine the position of the sensor. For example, passive positioning sensors may include optical markers that can be detected and tracked by an optical imaging system, such as an optical camera system used by a surgical navigation system.

As another example, a camera may be coupled to the x-ray source module 240 and/or the x-ray detector module 280, which may be used to optically detect passive positioning sensors 286 on the x-ray detector module 280 and/or the x-ray source module 246, respectively. In this way, optical alignment of the x-ray source module 240 and x-ray detector module 280 can be provided by optically tracking passive positioning sensors 246, 286 as the x-ray source module 240 and x-ray detector module 280 are moving.

In still other embodiments, cameras coupled to the x-ray source module 240 and/or x-ray detector module 280 can record images that are processed using AI (e.g., by a computer vision algorithm or other machine learning algorithm) to track their positions and maintain synchronous motion. Additionally or alternatively, such cameras can also detect and identify the subject 112, and can be analyzed to determine initial position data for aligning the x-ray source module 240 and x-ray detector module 280 with each and with the subject 112.

Additional cameras or other sensors (e.g., LIDAR sensors) may also be used to monitor the surrounding environment while the x-ray source module 240 and x-ray detector module 280 are moving to provide for object avoidance. If an obstacle (e.g., a person, surgical equipment, the patient table, etc.) is detected, the x-ray source module 240 and x-ray detector module 280 can be stopped to avoid a collision with the obstacle. When an obstacle is detected, the x-ray source 104 can also be automatically turned off as a safety measure.

In some instances, the x-ray source module 240 and x-ray detector module 280 may communicate position data acquired by the positioning sensors 246, 286 to one or more controllers, such as the control system 130, the x-ray controller 132, and/or the detector controller 136. Additionally or alternatively, the x-ray source module 240 and x-ray detector module 280 may communicate directly with one another. In these instances, the x-ray source module 240 and x-ray detector module 280 may share position data between each other in order to synchronously move along the first and second trajectories.

Position data may be communicated via wired connection, wireless connection, or both. In some embodiments, the x-ray source module 240 and x-ray detector module 280 can wirelessly communicate position data, or other data, via a wireless communication device (e.g., a transceiver) using a Bluetooth® protocol. In other embodiments, the wireless communication device communicates using other protocols (e.g., Wi-Fi®, Zigbee®, cellular protocols, a proprietary protocol, etc.) over a different type of wireless network. For example, the wireless communication device may be configured to communicate via Wi-Fi® through a wide area network such as the Internet or a local area network, or to communicate through a piconet (e.g., using infrared or NFC communications).

In addition to sharing position data measured by positioning sensors, the x-ray source module 240 and x-ray detector module 280 can maintain synchronous motion with each other based on x-rays transmitted by the x-ray source 104 and received by the x-ray detector 108.

Figure 3:
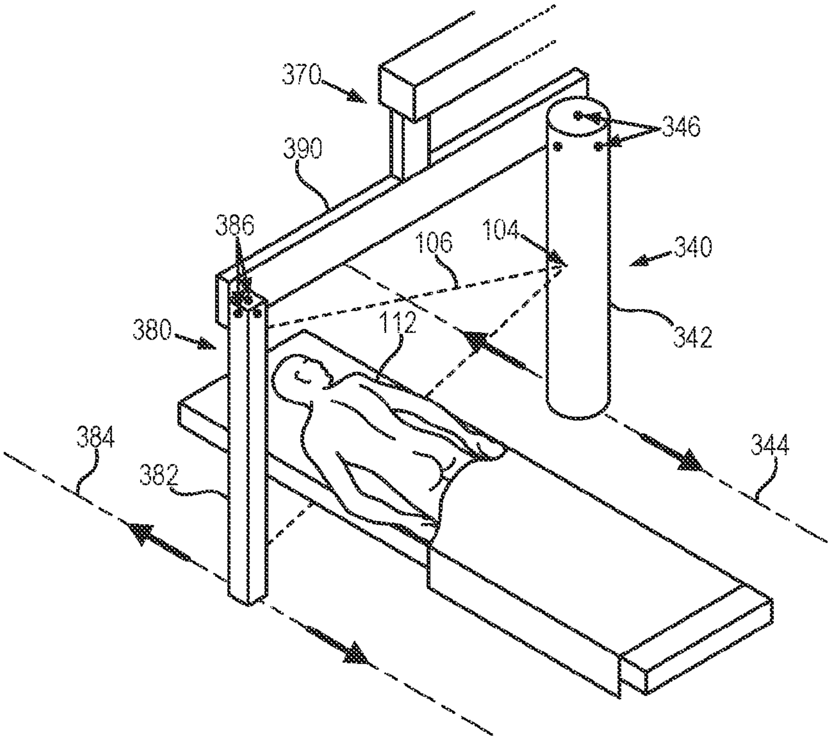
FIG. 3 shows an example linear scanning x-ray imaging system having physically coupled x-ray source and detector modules, according to some embodiments described in the present disclosure.

As noted above, in some configurations, the x-ray source and detector modules are physically coupled to each other. An example of such a configuration is illustrated in FIG. 3.

The imaging system 300 includes a moveable x-ray source module 340 and a moveable x-ray detector module 380 that is physically coupled to the x-ray source module 340. The x-ray source module 340 includes a housing 342 that contains or otherwise supports an x-ray source 104, whereas the x-ray detector module 380 includes a housing 382 that contains or otherwise supports an x-ray detector 108.

In the illustrated embodiment, a support member 390 coupled the x-ray source module 340 to the x-ray detector module 380. The support member 390 may include, for instance, a lateral support that is coupled to both the source module housing 342 and the detector module housing 382. In this way, the x-ray source module 340 and x-ray detector module 380 are physically coupled together, such that moving one will result in the other being moved in synchronization.

The support member 390 is coupled to one or more motion modules 370. As a non-limiting example, the motion module 370 can include a track or rail in the ceiling of the operating room, to which the support member 390 can be coupled, such as by a vertical coupling or the like. In other embodiments, the support member 390 can be coupled to a C-arm, an articulating arm, or other such support that can be coupled to a motion module 370 that include a track and/or rail on the ceiling and/or floor of the operating room. In still other examples, the support member 390 may be coupled to wheeled base modules, such as by vertically extending supports at each end of the support member 390.

During a scan to acquire x-ray projection data, the x-ray source module 340, and thus x-ray source 104, moves along the first trajectory 344 and the x-ray detector module, and thus x-ray detector 108, moves along the second trajectory 384, that is different from the first trajectory. The first and second trajectories 344, 384 may both be linear trajectories. The first and second trajectories 344, 384 may be parallel to each other. In some embodiments, the first and second trajectories 344, 384 may be oriented along the same direction, such that both the x-ray source module 340 and the x-ray detector module 380 are moved along the same direction (e.g., along the longitudinal direction) during a scan, albeit along different trajectories (e.g., a first trajectory 344 on one side of the subject 112 and a second trajectory 384 on another side of the subject 112). In other embodiments, the first and second trajectories 344, 384 may be oriented along different directions (e.g., first and second directions, respectively), such that the x-ray source module 340 and the x-ray detector module 380 are moved along different directions during a scan. For example, the x-ray source module 340 and the x-ray detector module 380 may in some configurations be rotated or partially rotated about a portion of the subject 112, such that the x-ray source 104 and the x-ray detector 108 move in different directions about the subject 112.

In some configurations, the x-ray source module 340 and x-ray detector module 380 can be rotated about the subject 112 to provide different view angles when scanning the subject 112. As one example, the x-ray source and detector modules 340, 380 can be rotated about the longitudinal axis to provide different view angles within the axial plane. In other examples, the x-ray source and detector modules 340, 380 can be rotated into different imaging planes, such as the sagittal plane, the coronal plane, or an oblique plane, which may be advantageous for localizing different anatomical targets.

The x-ray source module 340 and the x-ray detector module 380 can be in wired communication with each other, wireless communication with each other, or both. For instance, the x-ray source module 340 and x-ray detector module 380 may wirelessly communicate with each other to provide synchronous motion or otherwise share position data with each other.

The x-ray source module 340 can include source position sensors 346, and similarly the x-ray detector module 380 can include detector position sensors 386. The source position sensors 346 can be coupled to the housing 342 (e.g., arranged on, mounted to, or otherwise coupled to the housing 342) of the x-ray source module 340, and similarly the detector position sensors 386 can be coupled to the housing 382 (e.g., arranged on, mounted to, or otherwise coupled to the housing 382) of the x-ray detector module 380. The positioning sensors can record or otherwise measure the position of the source and/or detector modules, allowing for alignment of the x-ray source module 340 relative to the x-ray detector module 380 and the subject 112. Additionally, the position data recorded by or otherwise measured using the positioning sensors 346, 386 can be used to synchronize the motion of the x-ray source module 340 and the x-ray detector module 380.

The source and detector positioning sensors 346, 386 may be active positioning sensors, passive positioning sensors, or combinations thereof. As another example, a camera may be coupled to the x-ray source module 340, the x-ray detector module 380, and/or the support member 390, and which may be used to optically detect passive positioning sensors, the subject 112, or both. In this way, optical alignment of the x-ray source and detector modules 340, 380 with the subject can be provided by optically tracking passive positioning sensors, or through object detection of the subject 112 (e.g., by analyzing images with a computer vision algorithm or other machine learning algorithm).

In still other embodiments, cameras coupled to the x-ray source module 340, x-ray detector module 380, and/or support member 390 can record images that are processed using AI (e.g., by a computer vision algorithm or other machine learning algorithm) to track their positions and maintain synchronous motion. Additionally or alternatively, such cameras can also detect and identify the subject 112, and can be analyzed to determine initial position data for aligning the x-ray source module 340 and x-ray detector module 380 with each and with the subject 112. Additional cameras or other sensors (e.g., LIDAR sensors) may also be used to monitor the surrounding environment while the x-ray source module 340 and x-ray detector module 380 are moving to provide for object avoidance. If an obstacle is detected, the x-ray source module 340 and x-ray detector module 380 can be stopped to avoid a collision with the obstacle. When an obstacle is detected, the x-ray source 104 can also be automatically turned off as a safety measure.

Figure 4:
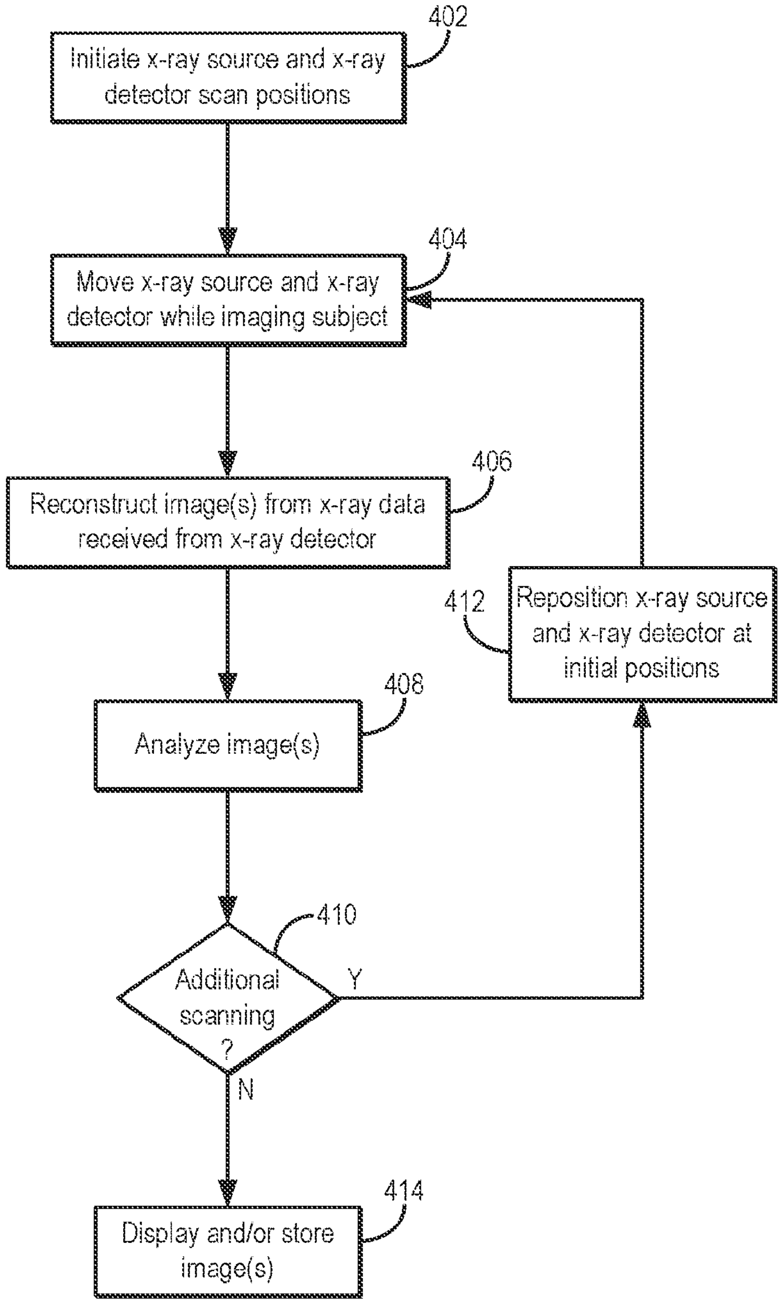
FIG. 4 is a flowchart illustrating the steps of an example method for imaging a patient using the x-ray imaging systems described in the present disclosure.

Referring now to FIG. 4, a flowchart is illustrated as setting forth the steps of an example method for using the imaging systems described in the present disclosure during a surgical procedure to identify the correct alignment or positioning of an anatomical target. For example, the imaging system can be used during a spinal surgery procedure to identify the correct vertebral level for a surgical procedure.

The method includes initiating the x-ray source and detector scan positions, as indicated at step 402. The x-ray source and detector modules can be moved to their initial positions manually, semi-autonomously, or autonomously.

In some instances, the x-ray source and/or detector modules can include a camera that is used to record images of the subject and/or the opposing imaging system module. By analyzing these images (e.g., using a computer vision algorithm), the source and detector modules can automatically determine their positions relative to each other and the subject, determine their initial positions relative to the subject, and then move themselves to those initial positions. As a non-limiting example, the x-ray source module may include a camera that records images of a scene containing the subject and the x-ray source detector module. A computer vision algorithm (e.g., an object detection algorithm, an image segmentation algorithm) can be used to process these images to detect the subject and the x-ray detector module and to determine their positions relative to the x-ray source module. Based on these position data, the initial scan positions can be determined.

In some other instances, positioning sensors on the x-ray source module and/or x-ray detector module can be used to determine the initial scan positions and to move the x-ray source and detector modules to those initial scan positions. As described above, the positioning sensors can be active sensors (e.g., RF transmitters and/or receivers, ultrasonic transmitters and/or receivers), passive sensors (e.g., optical fiducial markers), or combinations thereof.

The x-ray source and x-ray detector modules are then moved from their initial scan positions along the first and second, trajectories, respectively, while imaging the subject, as indicated at step 404. As described above, the x-ray source and detector modules are moved synchronously. In this way, x-ray projection data are acquired from the subject as the x-ray source and detector are translated along the first and second trajectories. As a non-limiting example, the first and second trajectories can be parallel with a longitudinal axis, such that the x-ray projection data are representative of axial images through the subject.

In some embodiments, while the x-ray source and detector modules are being moved, whether manually, semi-autonomously, or autonomously, position data are recorded and communicated between the x-ray source and detector modules. These position data are processed (e.g., by a central controller, by a dedicated controller or processor on the x-ray source module and/or detector module) to determine the relative positions of the x-ray source and detector modules, which can be used to control the motion of the modules and also to maintain synchronization between the modules.

One or more images are reconstructed from the x-ray projection data acquired by the x-ray detector, as indicated at step 406. In some implementations, the image(s) may be reconstructed in real time while the subject is being imaged during the imaging scan. In some other implementations, the image(s) may be reconstructed after the imaging scan is completed and the x-ray projection data have been completely acquired from the subject.

The reconstructed image(s) can be analyzed to evaluate the accuracy of a procedure, to confirm the location of and/or alignment with an anatomical target (e.g., a particular spinal level), and so on, as indicated at step 408. As a non-limiting example, the image(s) can be analyzed by a computer system to generate a quantitative parameter that measures the alignment and/or relative angle of the spine or other anatomy. The quantitative parameter can be used to evaluate the accuracy of a spinal surgery procedure or other orthopedic surgery procedure. If the quantitative parameter indicates that the spine or other anatomy is not properly aligned following the surgical procedure, then the surgeon can make adjustments while the patient is still in the operating room. Advantageously, this allows for real-time feedback of surgical procedure accuracy while the patient is still in the operating room, allowing for intraoperative corrections to be identified and made, thereby reducing the need for multiple procedures.

In some implementations, additional scanning of the subject may be desired. For instance, multiple scans may be performed during a surgical procedure to track progress during the procedure and to confirm agreement of the subject's anatomy with a surgical plan. Additionally or alternatively, when analyzing the image(s) acquired from the subject indicate that the alignment of the spine or other anatomy needs correction, additional scanning can be performed after intraoperative corrections are made to confirm accurate alignment of the spine or other anatomy.

When additional scanning is desired, as indicated at decision block 410, the x-ray source and x-ray detector can be repositioned to initial scanning positions (or to new initial scan positions), as indicated at step 412. Additional x-ray data are then acquired by rescanning the subject, from which one or more additional images can be reconstructed and optionally analyzed. Otherwise, the reconstructed image(s) can be displayed to a user and/or stored for later use or processing, as indicated at step 414.

The present disclosure has described one or more preferred embodiments, and it should be appreciated that many equivalents, alternatives, variations, and modifications, aside from those expressly stated, are possible and within the scope of the invention.

The invention claimed is:

1. An x-ray imaging system, comprising:

an x-ray source housed in an x-ray source housing configured to be translated along a first trajectory;

an x-ray detector housed in an x-ray detector housing configured to be translated along a second trajectory that is different from the first trajectory, wherein the x-ray detector housing is physically uncoupled from the x-ray source housing; and a controller in communication with the x-ray source and the x-ray detector, wherein the controller is configured to:

align, using an artificial intelligence algorithm, the x-ray source with the x-ray detector; and synchronously move the x-ray source along the first trajectory and the x-ray detector along the second trajectory.

2. The x-ray imaging system of claim 1, wherein the first trajectory and the second trajectory are both linear scanning trajectories.

3. The x-ray imaging system of claim 2, wherein the first trajectory is parallel to the second trajectory.

4. The x-ray imaging system of claim 1, wherein the artificial intelligence algorithm comprises a machine learning algorithm.

5. The x-ray imaging system of claim 4, wherein the machine learning algorithm implements a computer vision algorithm.

6. The x-ray imaging system of claim 1, wherein the x-ray source is movably coupled to a first rail that defines the first trajectory, such that as the x-ray source is translated along the first rail the x-ray source is translated along the first trajectory.

7. The x-ray imaging system of claim 6, wherein the x-ray detector is movably coupled to a second rail that defines the second trajectory, such that as the x-ray source is translated along the second rail the x-ray source is translated along the second trajectory.

8. The x-ray imaging system of claim 6, wherein the first rail is a floor-mounted rail.

9. The x-ray imaging system of claim 8, wherein the second rail is a floor-mounted rail.

10. The x-ray imaging system of claim 1, wherein the x-ray source is coupled to a moveable base module that is configured to translate along a surface.

11. The x-ray imaging system of claim 10, wherein the base module comprises a wheeled base module that is configured to roll along the surface.

12. The x-ray imaging system of claim 1, wherein the x-ray detector is coupled to a moveable base module that is configured to translate along a surface.

13. The x-ray imaging system of claim 1, wherein at least one of the x-ray source or the x-ray detector includes at least one positioning sensor that is configured to generate positioning data, wherein the controller is configured to receive the positioning data from the at least one positioning sensor and to align the x-ray source with the x-ray detector based on the positioning data.

14. The x-ray imaging system of claim 13, wherein each of the x-ray source and the x-ray detector includes at least one positioning sensor.

15. The x-ray imaging system of claim 13, wherein the at least one positioning sensor comprises at least one of an optical positioning sensor, a radio frequency (RF)-based positioning sensor, or an inertial positioning sensor.

16. The x-ray imaging system of claim 1, wherein the controller is housed within one of the x-ray source housing or the x-ray detector housing.

17. The x-ray imaging system of claim 1, wherein the controller is configured to:

receive x-ray projection data acquired by the x-ray detector;

reconstruct an image from the x-ray projection data; and analyze the image to determine a quantitative parameter measuring alignment and relative angle of a spine of a subject as depicted in the image.

18. An x-ray imaging system, comprising:

an x-ray source housed in an x-ray source housing configured to be translated along a first trajectory;

an x-ray detector housed in an x-ray detector housing configured to be translated along a second trajectory that is different from the first trajectory, wherein the x-ray detector housing is physically uncoupled from the x-ray source housing and wherein the x-ray detector comprises a linear detector array; and a controller in communication with the x-ray source and the x-ray detector, wherein the controller is configured to:

align the x-ray source with the x-ray detector; and synchronously move the x-ray source along the first trajectory and the x-ray detector along the second trajectory.

19. An x-ray imaging system, comprising:

an x-ray source module comprising:

a first housing;

an x-ray source housed within the first housing; and a first wheeled base coupled to the first housing;

an x-ray detector module comprising:

a second housing;

an x-ray detector housed within the second housing; and a second wheeled base coupled to the second housing;

a processor in communication with the x-ray source and the x-ray detector, wherein the processor is configured to:

automatically align, using an artificial intelligence algorithm, the x-ray source module with the x-ray detector module by controlling the first wheeled base and the second wheeled base to move the x-ray source module and the x-ray detector module to initial scan positions; and control the first wheeled base and the second wheeled base to synchronously move the x-ray source module along a first trajectory and the x-ray detector module along a second trajectory that is different from the first trajectory.

* * * * *